US010311977B2

(12) United States Patent
Huff et al.

(10) Patent No.: US 10,311,977 B2
(45) Date of Patent: Jun. 4, 2019

(54) PROACTIVE DISEASE STATE MANAGEMENT SYSTEM

(71) Applicant: Huff & Day Enterprises, LLC, Loveland, CO (US)

(72) Inventors: Randy Blane Huff, Loveland, CO (US); William Glynn Day, Baton Rouge, LA (US)

(73) Assignee: Huff & Enterprises, LLC, Loveland, CO (US)

( * ) Notice: Subject to any disclaimer, the term of this patent is extended or adjusted under 35 U.S.C. 154(b) by 1 day.

(21) Appl. No.: 15/898,135

(22) Filed: Feb. 15, 2018

(65) Prior Publication Data

US 2018/0233231 A1    Aug. 16, 2018

Related U.S. Application Data

(60) Provisional application No. 62/460,014, filed on Feb. 16, 2017.

(51) Int. Cl.
| | | |
|---|---|---|
| *G16H 50/30* | (2018.01) | |
| *G16H 50/70* | (2018.01) | |
| *G16H 10/60* | (2018.01) | |

(52) U.S. Cl.
CPC .............. *G16H 50/30* (2018.01); *G16H 10/60* (2018.01); *G16H 50/70* (2018.01)

(58) Field of Classification Search
CPC ........ G16H 10/60; G16H 50/70; G16H 20/10; G16H 40/63; G16H 50/30; G06F 17/271;
(Continued)

(56) References Cited

U.S. PATENT DOCUMENTS

2003/0167189 A1*  9/2003  Lutgen ................. G06F 19/322
                                                                    705/3
2012/0271612 A1   10/2012  Barsoum et al.
(Continued)

FOREIGN PATENT DOCUMENTS

WO    2006/130361    12/2006
WO    2016/022437     2/2016
(Continued)

OTHER PUBLICATIONS

PCT International Patent Application No. PCT/US18/18518; International Search Report and Written Opinion of the International Searching Authority dated Apr. 19, 2018, 13 pages.
(Continued)

*Primary Examiner* — Maroun P Kanaan
(74) *Attorney, Agent, or Firm* — Craig R. Miles; CR Miles P.C.

(57) ABSTRACT

A proactive disease state management system including network elements, computer elements and software elements operable to support a plurality of subscriber devices each under a subscription plan in which the subscriber device requests the collection of electronic medical records of a patient for evaluation by a proactive disease state management engine which interrelates patient information, patient medical information and patient laboratory information included in the electronic medical record of a patient to generate engine result data and populate the fields of a request reply to the subscriber device.

6 Claims, 5 Drawing Sheets

(58) Field of Classification Search
CPC .... G06F 17/3043; G06F 19/00; G06F 19/328; G06F 19/324; G06F 17/3053; G06F 19/3418; G06F 19/3456; G06Q 50/24; G06Q 10/06393
See application file for complete search history.

(56) References Cited

U.S. PATENT DOCUMENTS

| | | |
|---|---|---|
| 2015/0024961 A1 | 1/2015 | Klass et al. |
| 2015/0046182 A1* | 2/2015 | Kinney ................. G16H 10/60 705/3 |
| 2015/0095046 A1* | 4/2015 | Pironti ............... G06F 19/3431 705/2 |
| 2015/0379241 A1* | 12/2015 | Furst .................. G06F 17/2705 705/3 |
| 2017/0004274 A1 | 1/2017 | Mehta et al. |

FOREIGN PATENT DOCUMENTS

| | | |
|---|---|---|
| WO | 2016/059602 | 4/2016 |
| WO | 2016/141045 | 9/2016 |

OTHER PUBLICATIONS

U.S. Appl. No. 62/460,014, filed Feb. 16, 2017.

* cited by examiner

PROACTIVE DISEASE STATE MANAGEMENT SYSTEM

This U.S. Non-Provisional patent application claims the benefit of U.S. Provisional Patent Application No. 62/460,014, filed Feb. 16, 2017, hereby incorporated by reference herein.

I. FIELD OF THE INVENTION

A proactive disease state management system which correlates data included in the electronic medical record of a patient to a plurality of disease states contained in a disease state database and calculates a score attributable to each one of the plurality of disease states contained in the disease state database based on correlations made between the data in the electronic medical record and the plurality of disease states, and further calculates an aggregate score for all correlations to the disease states contained in the disease state database which can by comparison of the aggregate score to an average aggregate score be assigned a risk level attributable to the electronic medical record of the patient.

II. SUMMARY OF THE INVENTION

A broad object of embodiments of the invention can be to provide a proactive disease state management system including network elements, computer elements and software elements operable to support a plurality of subscriber devices each under a subscription plan in which the subscriber device requests the collection of electronic medical records of a patient for evaluation by a proactive disease state management program which correlates International Statistical Classification of Diseases and Related Codes ("ICDC") or National Drug Codes ("NDC") included in the electronic medical record of a patient to a plurality of disease states included in a disease state database and calculates a score attributable to each one of the plurality of disease states contained in the disease state database, and further calculates an aggregate score for all the correlations made to disease states contained in the disease state database which can be by comparison of the aggregate score to an average aggregate score can be assigned a risk level attributable to the electronic medical record of the patient.

Another broad object of embodiments of the invention can be to provide a method in a computer implemented proactive disease state management system including one or more of: retrieving an electronic medical record from an electronic medical records database and evaluating the medical record by identifying each ICDC or NDC in the electronic medical record and identifying matches between the ICDC or the NDC to said plurality of disease states in a disease state database and scoring said electronic medical record of a patient by aggregating the positive score values associated with each of the plurality of disease states in the disease state database and assigning the aggregate health score to a risk level based on said comparison of the aggregate score to an average aggregate score.

Naturally, further objects of particular embodiments of the invention are disclosed throughout other areas of the specification, drawings, and claims.

IV. DETAILED DESCRIPTION OF THE INVENTION

Proactive Disease State Management System.

Generally referring to FIGS. 1 through 5, the proactive disease state management system (1)("PDSMS") includes network elements, computer elements and software elements operable to support a plurality of subscriber devices (2) each under a subscription plan (3) in which the subscriber device (2) requests the collection of electronic medical records (4)("EMR") of a patient (5) and evaluation of the EMR (4) by a proactive disease state management engine(s)(6)("PDSME" or "engine") which interrelates one or more of patient information (7), patient medical information (8) and patient laboratory information (9) included in the EMR (4) to generate engine result data (10) and populate the fields of a request reply (11) to the subscriber device (2).

The Network.

Figure 1:
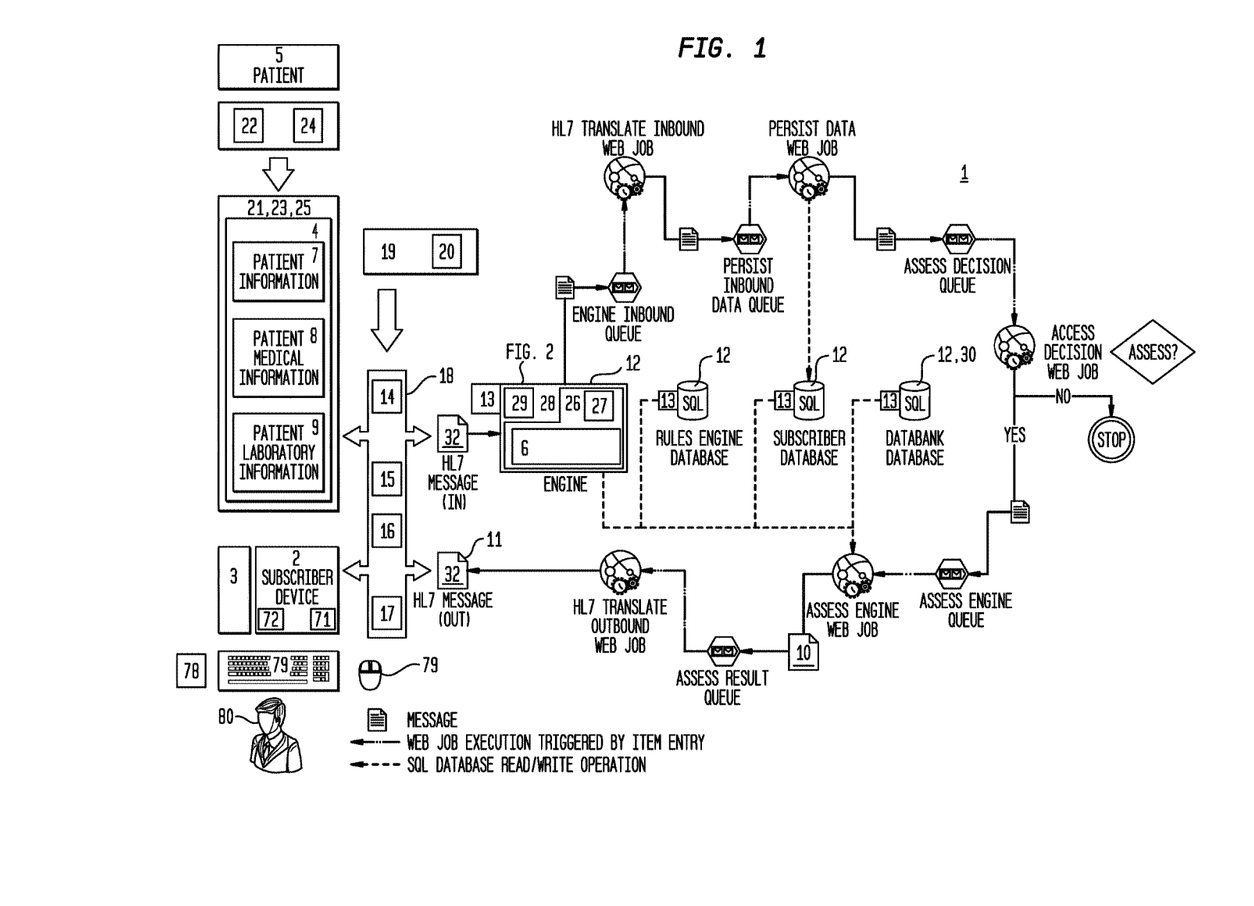
FIG. 1 is a block diagram of a particular embodiment of a proactive disease state management system.
Figure 2:
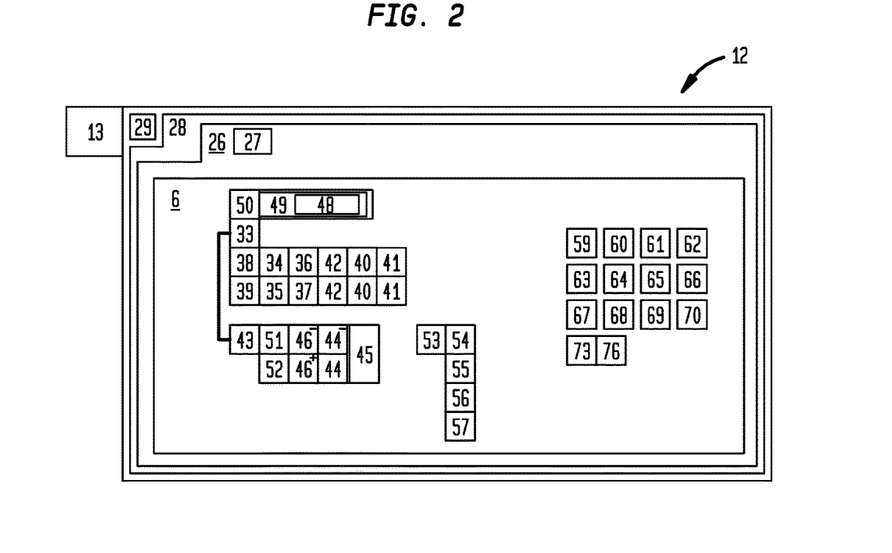
FIG. 2 is an enlarged portion of FIG. 1 showing a processor communicably coupled to a non-transitory computer readable media containing a particular embodiment of the proactive disease state management program.
Figure 3:
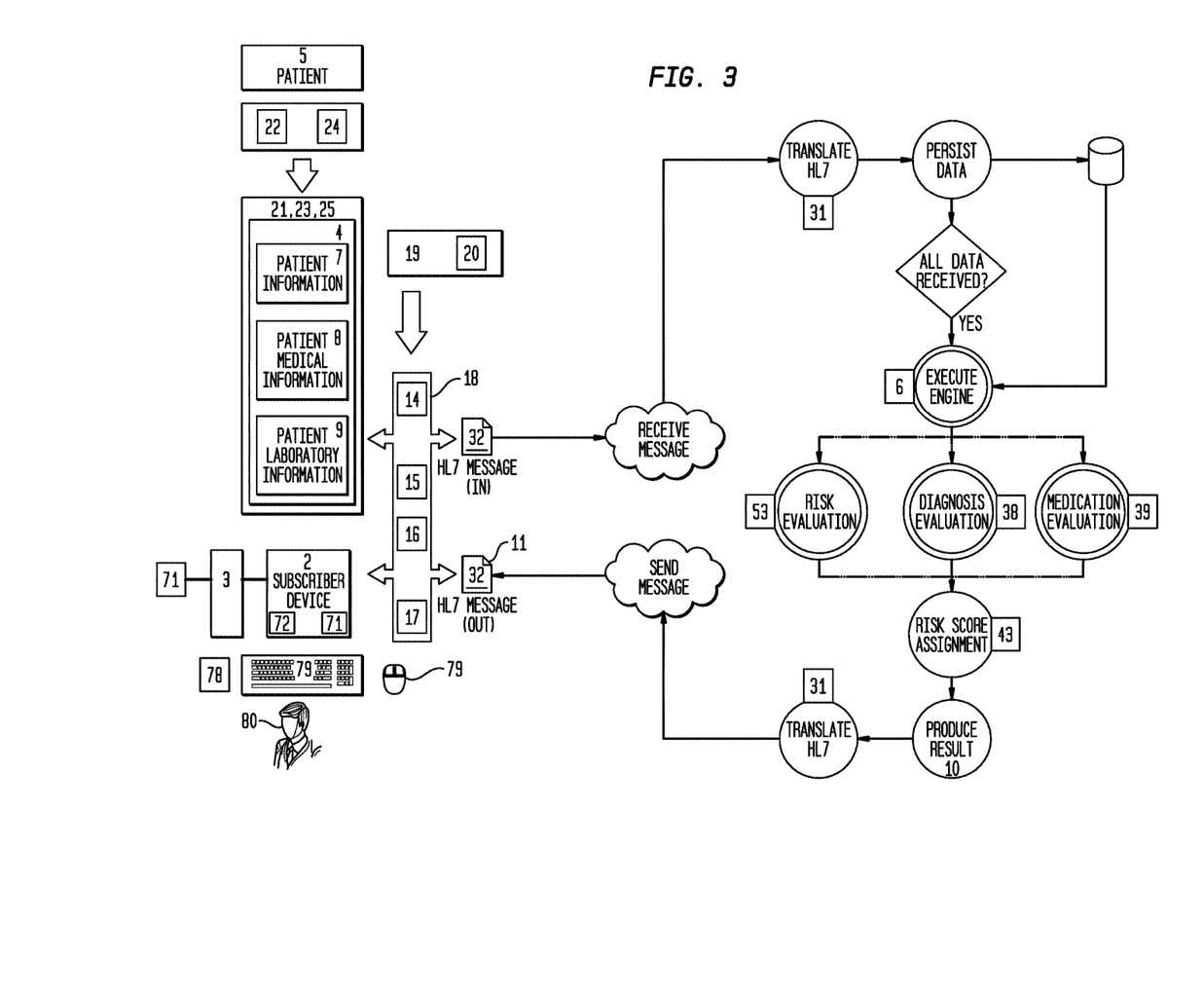
FIG. 3 is a block flow diagram illustrating a method in the proactive disease state management system of evaluating and scoring the data in an electronic medical record.

Now referring primarily to FIGS. 1 and 2, the PDSMS (1) (also referred to as the "system") can be distributed on one or more servers (12) (along with associated databases 12' and 30) having a server network interface (13) operably coupled to a plurality of subscriber devices (2) by a public network (14), such as the Internet (15), a cellular-based wireless network(s) (16), or a local network (17)(individually or collectively the "network" (18)).

The network (18) supports a plurality of communication resources (19)(along with other communication resources made available in the future) to afford as illustrative examples: recording, transmission, or reproduction of images (whether still or moving images), sound relating to acoustical, mechanical or electrical frequencies, electronic mail, instant messaging, text messaging (such as short message service) multimedia messaging (such as multimedia message service) attributable to the execution of self-contained programs or pieces of software designed to fulfill particular purposes (also referred to as "applications" (20)), as illustrative examples: web applications, online applications, mobile applications, downloadable by a subscriber device (2).

Remote Patient Medical Information Databases.

A patient's EMR (4) can be stored in one or more medical records databases (21). The term "electronic medical record (EMR)" refers to the record of patient encounters and medical services received by one of a plurality of patients (5) from one or more care delivery organizations (22) which can each occur in a common format using a common clinical data repository (23) or can be an accumulation of EMR (4) of a plurality of unaffiliated care delivery organizations (24) which in turn utilize unaffiliated clinical data repositories (25) which may not be in a common format. The EMR (4)

of a patient (5) includes, but need not necessarily be limited to, patient information (7) such as date of birth, weight, sex; patient medical information (8) such as current diagnosis, prescribed medications and allergy indications; and patient laboratory information (9) such as performed laboratory tests and laboratory test values.

Health Level 7 Data Files.

Typically, the transfer of EMR (4) between software applications used by care delivery organizations (22)(24) occurs in accordance with a set of international standards referred to as the Health Level 7 ("HL7") standards. These standards focus on the application layer, which is "layer 7" in the Open Systems Interconnection Model ("OSI model"). The HL7 standards are produced by Health Level Seven International, an international standards organization, and are adopted by other standards issuing bodies such as American National Standards Institute and International Organization for Standardization.

HL7 specifies a number of flexible standards, guidelines, and methodologies by which a plurality of healthcare delivery organizations (23)(24) can communicate with each other. HL7 guidelines or data standards are a set of rules that allow information to be shared and processed in a uniform and consistent manner. These data standards are meant to allow health care delivery organizations to easily share clinical information.

HL7 I considers the following standards to be its primary standards:

Version 2.x Messaging Standard—an interoperability specification for health and medical transactions.

Version 3 Messaging Standard—an interoperability specification for health and medical transactions.

Clinical Document Architecture (CDA)—an exchange model for clinical documents, based on HL7 Version 3.

Continuity of Care Document (CCD)—a US specification for the exchange of medical summaries, based on CDA.

Structured Product Labeling (SPL)—the published information that accompanies a medicine, based on HL7 Version 3.

Clinical Context Object Workgroup (CCOW)—an interoperability specification for the visual integration of user applications.

PDSMS Web Application Program Interface.

Embodiments of the PDSMS includes a PDSMS Web application program interface ("PDSMS Web API") (26). The PDSMS Web API (26) includes an PDSMS web interface program (27) contained in a non-transitory computer readable media (28)(also referred to as a memory element) communicatively coupled to a processor (29). Upon execution, the PDSMS Web API (26) routes hypertext transfer protocol ("HTTP") requests to the one or more medical records databases (21) to transfer the requested EMR (4) of a patient (5) to the PDSME database (12'), (30) for evaluation by the PDSME (6).

The Engine.

Embodiments of the PDSMS (1) can include a proactive disease state management engine ("PDSME" or "program") (6) contained in the memory element (28) communicatively coupled to the processor (29). The PDSME includes computer-executable instructions in the form of a program and modules that utilize routines, objects, components, data structures, or the like, to perform particular functions or tasks or implement particular abstract data types, or the like, being executed by the computer elements and network elements, it is not intended that embodiments of the invention be limited to a particular set of computer-executable instructions or protocols.

The HL7 Translation Module.

Embodiments of the PDSME (6) can include an HL7 translation module (31) executable to translate HL7 data files (32) contained in the EMR (4) of a patient (5) retrieved from one or more medical records databases (21) of one or more common clinical data repositories (23), or one or more unaffiliated clinical data repositories (24) (or a combination thereof) into a common format which can be downloaded to a PDSME database (30). Similarly, the HL7 translation module (31) can be executed to translate the result data (10) from the PDSME (6), or contained in the PDSME database (30), from the common format of the PDSME database (30) to HL7 data files (32) for transmission to one or more subscriber devices (2).

EMR Evaluation Module.

Embodiments of the PDSME (6) further include a EMR evaluation module (33). The EMR evaluation module (33) can be executed to evaluate the EMR (4) of a patient (5) to identify International Statistical Classification of Diseases and Related Codes (34) ("ICDC") the ("Diagnosis Evaluation") (38) and to identify National Drug Codes (35) ("NDC") (the "Medication Evaluation") (39). The ICDC (34) includes more than 14,400 different codes each associated with and allows tracking of diagnosis of the corresponding disease state (36). The NDC (34) is a ten digit, three-segment identifier associated with and allows the tracking of each medication (37) listed under Section 510 of the US Federal Food, Drug, and Cosmetic Act. While embodiments of the invention may describe the use of ICDC and NDC as practiced in the United States; it is not intended to preclude embodiments which use classification systems similar to the ICDC or NDC in foreign countries.

The EMR evaluation module (33) operates on the PDSME database (30) in which each of a plurality of disease states (36) can be associated with one or more ICDC (34) or NDC (35). In part, the EMR evaluation module (33) operates to perform a Diagnosis Evaluation (38) in which the one or more ICDC (34) identified in the EMR (4) of a patient (5) can be compared against each of a plurality of disease states (36) contained in the PDSME database (30) and by comparison can be matched to a disease state (36) to trigger a "YES" indicator (40) or not matched to a diseases state to trigger a "NO" indicator (41) associated with each disease state (36). The "YES" indicator (40) establishes that either a diagnosis for the disease state (36) occurs as a ICDC (34) in the EMR (4) of the patient (5) or other diagnoses occur as a ICDC (34) in the EMR (4) of the patient (5) that could contribute to exacerbation or generation of the disease state (34). Also in part, the EMR evaluation module (33) operates on the PDSME database (30) to perform the Medication Evaluation (39) in which the one or more of the NDC (35) identified in EMR (4) of a patient (5) can be compared against the plurality of disease states (36) and by comparison can be matched to a disease state (36) to trigger a "Yes" indicator (40) or not matched to trigger a "NO" indicator (41).

As one illustrative example, the relational PDSME database (30) can contain a plurality of disease states (36) each associated with a plurality of ICDC (34) or NDC (35) (collectively referred to as "triggers" (42) that match to the ICDC (34) or NDC (35) (or both) occurring in the EMR (4) of a patient (5). As one non-limiting example, an embodiment of the PDSME database (30) can include:

Sleep Disorder—having an associated total of 84 triggers

Stroke having an associated total of 23 triggers

Urinary Tract Infections having an associated total of 48 triggers

Parkinson's having an associated total of 43 triggers
Pain having an associated total of 34 triggers
Osteoporosis having an associated total of 36 triggers
Heart Failure having an associated total of 25 triggers
Gastrointestinal having an associated total of 53 triggers
Falls having an associated total of 35 triggers
Depression having an associated total of 35 triggers
Dehydration having an associated total of 28 triggers
COPD having an associated total of 42 triggers
Altered Nutritional Status having an associated total of 80 triggers
Diabetes having an associated total of 83 triggers As one particular example, the disease state (36) "Altered Nutritional Status" can be contained in the PDSME database (30). The administrator of the PDSME (6) can associate a plurality of ICDC (34) and a plurality of NDC (35) with the disease state (36) "Altered Nutritional Status" as triggers (42). The ICDC (34) or NDC (35) associated with the disease state (36) as triggers (42) can be identified by the administrator using appropriate clinical guidelines. The Institute of Medicine defines clinical practice guidelines as "statements that include recommendations, intended to optimize patient care, that are informed by a systematic review of evidence and an assessment of the benefits and harms of alternative care options." One source of clinical guidelines can be American College of Physicians. Accordingly, the ICDC (34) and the NDC (35) associated with a disease state (36) can be greater or lesser in based on changes in clinical guidelines over time. Accordingly, the total number of triggers (42) associated with each disease state (36) can vary over time.

The Scoring Module.

Embodiments of the PDSME (6) further include a EMR scoring module (43) communicatively coupled to the EMR evaluation module (33). The EMR scoring module (43) can be executed to calculate and attribute a score (44) to each one of the plurality of disease states (36) contained in the PDSME database (30), and can calculate an aggregate score (45) for all the disease states (36) contained in the PDSME database (36) (also referred to as the "health score" (45). The health score (45) provides a clinician a ready reference regarding the health level of each patient (5).

As to particular embodiments, including the Diagnosis Evaluation (38), if the EMR evaluation module (33) matches an ICDC (34) to a disease state (36) contained in the PDSME database (30) and associates a disease state indicator of "Yes" (40) to the disease state (36), then the EMR scoring module (43) associates a score value (46) of "one" with that listed disease state (36), and if the EMR evaluation module (33) fails to match an ICDC (34) to a disease state (36) contained in the PDSME database (30) and associates a disease state indicator "No" (41) to the disease state (36), then the EMR scoring module (43) associates a score value (46) of "zero" (also referred to as a "null score value") or with that listed disease state (36).

As to particular embodiments, including the Medication Evaluation (39), if the EMR evaluation module (33) matches an NDC (35) to a disease state (36) contained in the PDSME database (30) and associates a disease state indicator of "Yes" (30) with that listed disease state (36), and if, the EMR evaluation module (33) further matches the medication (37) associated with the NDC (35) to an adverse effect on the disease state (36), or if the medication (37) associated with the NDC (35) contributes or potentiates in the development of the disease state (36) (collectively "an adverse effect"), then the EMR scoring module (43) associates a score value (46) of "one" with the disease state (36), if in the alternative, the EMR evaluation module (33) further matches the medication (37) associated with the NDC (35) also matched to the disease state (36), then the EMR scoring module (43) associates a score value (46) of "zero" with the disease state (36), if however, the EMR evaluation module (33) does not match a NDC (35) to a disease state (36) contained in the PDSME database (30) and associates a disease state indicator of "No" (41) with the disease state (36), then the EMR scoring module (43) associates a score value (46) of "zero" to the disease state (36), if however, if the EMR evaluation module (33) matches an ICDC (34) to the disease state (36), and if the EMR evaluation module (33) does not match an NDC (35) to the disease state (36) and associates a disease state indicator "Yes" (40) to the disease state (36), then the EMR scoring module (43) associates a score value (46) of "one" to the disease state (36) for not treating the disease state (36).

As to the particular embodiments above described, due to the complexity of individual physiological response to medications (37) and other existing disease states (36), there are no other factors weighed in assigning the score values (46) as described above.

The Rules Engine.

The above illustrative examples of the EMR evaluation module (33) and the EMR scoring module (43) are not intended to preclude other rule-based embodiments which allow the EMR (4) of a patient (5) to be evaluated based on other EMR data (47) that in accordance with the general hierarchy of the rules (48) contained the knowledge base (49) of the rules engine (50).

As to embodiments, the rules engine (50) has a hierarchy as follows:

I. Disease State(s) contained in the PDSME database (30).
   A. Trigger Rule—a disease state(s)(36) is determined if an ICDC (34) is contained in the EMR (4) of a patient (5).
   B. Groups—groupings/roll-ups of similar rules (the subheadings within the documents)
      1) "Risk" if EMR data (47) in the EMR (4) is associated with a health risk (51) of a disease state (36), then that hit is assigned a score value (46) which is positive (the above illustrative embodiments assign one "1");
      2) "Therapy" if a EMR data (47) in the EMR (4) is associated with a therapy (52) of a disease state (36), then that hit is assigned a score value (46) which is negative (the above illustrative embodiments assign minus one "−1").

As an example, for the disease state (36) "Altered Nutritional Status" the rules engine (50) includes the follow rules:
I. Disease State: Altered Nutritional Status ("ANS").
   A. Trigger Rule: EMR (4) of patient (5) includes the ICDC (34) for ANS
      Group: "Altered Nutritional Status Dysphagia Side Effect Meds"
         Rule: "ACE Inhibitors" (37); "Risk" (51); "Score"=1
      Group: "Altered Nutritional Status Acceptable Meds"
         Rule: "Megace" (37); "Therapy" (52); "Score"=−1

The PDSME Report.

Now referring primarily to the illustrative example of Table 1, the EMR evaluation module (33) can be executed to evaluate the EMR (4) of a patient (5) to compare ICDC (34) and NDC (35) against fifteen disease states (36)(as shown in Table 1, Column 1—Disease States; however, the example of the fifteen disease states (36) listed in Table 1 is not intended to preclude embodiments which include a greater or lesser number of disease states (36). One or more "triggers (42)" can be associated with each disease state (36) (as shown in Table 1, Column 2—Actual Risk Factor Trigger Totals) and in the example of Table 1 there are a total of 695 triggers (42) associated with the fifteen disease states (36); however, this is not intended to preclude embodiments have a greater or lesser number of triggers (42) for each disease state (36) or in aggregate total for all the disease states (36) listed. The EMR evaluation module (33) scores the disease state indicators (40)(41) (as shown in Table 1, Column 3—Patient Total) and then calculates the score (44) for each disease state (36)(Patient Total For Disease State÷by Risk Factor Trigger Total For Disease State×100) and in the aggregate for the listed plurality of disease states (36)(Patient Total For All Disease States÷by Risk Factor Trigger Total for All Disease States×100) to generate the health score (45). In the example of Table 1 the aggregate health score (45) is calculated by the EMR scoring module (43) (695÷467×100=67).

TABLE 1

EXAMPLE HEALTH SCORE REPORT.

| Disease States (36) | Actual Risk Factor Trigger Totals (RF) | Patient Total (PT) | Health SCORE (100 × PT/RF) |
|---|---|---|---|
| Sleep Disorder | 84 | 23 | 27 |
| Stroke | 23 | 18 | 78 |
| Urinary Tract Infection | 48 | 41 | 85 |
| Parkinson's | 43 | 34 | 79 |
| Pain | 34 | 21 | 62 |
| Osteoporosis | 36 | 31 | 86 |
| Heart Failure | 25 | 13 | 52 |
| Gastrointestinal Disorder | 53 | 45 | 85 |
| Fall | 35 | 23 | 66 |
| Depression | 35 | 21 | 60 |
| Dementia | 46 | 43 | 93 |
| Dehydration | 28 | 11 | 39 |
| COPD | 42 | 33 | 79 |
| Altered Nutritional Status | 80 | 65 | 81 |
| Diabetes | 83 | 45 | 54 |
| Total Overall | 695 | 467 | 67 (Health Score) |

The Patient Risk Level Assignment Module.

Embodiments of the PDSME (6) further include a patient risk level assignment module (53) which operates to assign each of a plurality of patients (5) to a risk level (54) of: a high risk level (55), a median risk level (56), or a nominal risk level (57). The segregation of patients (5) into risk levels (54) applies to those patient's (5) identified by the EMR evaluation module (33) as having a "YES" indicator (40) indicating an ICDC (34) in the EMR (4) for any one of the plurality of disease states (36) contained in the PDSME database (30). The patients (5) can then be allocated to a risk level (54) based comparison of the aggregate health score (45) to the average aggregate health score (58) of all patients (5) in a bell curve format divided into one-thirds with the higher third comprising high risk level (55), the middle third comprising the median risk level (56) and the lower third comprising the nominal risk level (57). Patients (5) not having a ICDC (34) in the EMR (4) for all of the plurality of disease states (36) contained in the PDSME database (36) are assigned to the nominal risk level (57). All patients that have an existing ICDC (34) in the EMR (4) are automatically assigned to the high risk level (55).

Counseling Engine.

Embodiments of the PDSME (6) can, but need not necessarily, further include a counseling engine (59) executable to assist clinicians in counseling the patient (5), with a corresponding set for the professional. It can serve as both a reminder and a reliable reference resource for clinicians with only important information highlighted.

Min/Max Dose Engine.

Embodiments of the PDSME (6) can, but need not necessarily, include a minimum-maximum dose engine (60) executable to provide drug-dosing information to clinicians on the most frequently prescribed drugs. This five-engine set offers an easy to implement resource for quick-check information on the usual range of daily doses for adult, pediatric, and geriatric patients.

Dosage Range Check Engine.

Embodiments of the PDSME (6) can, but need not necessarily, include a dosage range check engine (61) executable to monitor the appropriateness of medication dosing. It uses age, route of administration, indications, and organ function data to identify safe dosage levels based on certain patient-specific parameters. It provides renal dose screening, hepatic adjustment indicators, and lifetime maximum dose. Dosing information also accommodates the narrow therapeutic window for neonates and infants.

Drug-Disease Contraindications Engine.

Embodiments of the PDSME (6) can, but need not necessarily, include a drug-disease contraindications engine (62) executable to create warnings concerning the use of certain medications in patients with specific conditions and diseases, or patients who have had certain procedures or diagnostic tests. Clinicians may use these warnings to make informed decisions about altering a patient's drug therapy when these conditions exist.

Prioritized Warnings Engine.

Embodiments of the PDSME (6) can, but need not necessarily, include a prioritized warnings engine (63) executable to provide auxiliary labels and establishes label priority for a particular drug product based on the relative clinical importance of the message for that particular clinical formulation. These label warnings enable clinicians to provide patients with essential information by affixing the labels to the medication vial, or printing them separately for reference.

Indications Engine.

Embodiments of the PDSME (6) can, but need not necessarily, include an indications engine (64) executable to assessing the appropriateness of drug therapy for a specific medical condition, based on current medical evidence. This engine provides clinicians information to make informed decisions regarding medication therapy and may also be used to help identify potentially inappropriate drug treatment for a given disease. The engine includes both FDA-approved and certain "off-label" indications substantiated by primary medical literature.

Drug Information Engine.

Embodiments of the PDSME (6) can, but need not necessarily, include a drug information engine (65) executable to provide an evidence-based foundation for safe and effective drug therapy. These full-text monographs have been officially designated as a federal standard on drug therapy, based on accepted medical practice, and are used by pharmacists, physicians, nurses, and other clinicians in a wide range of healthcare environments.

High Risk Medication Engine.

Embodiments of the PDSME (6) can, but need not necessarily, include a high risk medication engine (66) executable to provide risk evaluation and mitigation strategy (REMS) and boxed warning information of prescription drugs directly within the user's workflow. The engine reviews REMS and boxed warnings, captures important and actionable content and presents it in a format that is flexible and easy to integrate, eliminating the manual effort it takes to monitor REMS and boxed warning changes from the manufacturer. The engine also maintains historical Information to support retrospective analysis or audit functions. This engine helps ensure patient safety and regulatory compliance set forth by the FDA by presenting actionable messages to the right user at the right time.

Medication Guide Engine.

Embodiments of the PDSME (6) can, but need not necessarily, include a medication guide engine (67) is a convenient source for all currently available Medication Guides submitted by manufacturers through the FDA Structured Product Label (SPL) file and subsequently posted to the National Library of Medicine's (NLM) "Daily Med" website. Through validated links to the National Drug Code (NDC) in the engine provides a notification to pharmacists when a Medication Guide is required for a drug product and provides automated access to all electronic Medication Guides filed with the FDA, in PDF and XML.

Drug-Lab Interference Engine.

Embodiments of the PDSME (6) can, but need not necessarily, include a drug-lab interference engine (68) executable identify drugs that may falsely alter laboratory test results. A drug can falsely alter a laboratory test result by causing an analytic interference in a laboratory test. This engine can be used by clinicians to screen patient lab and drug therapy data, and to look up reference information on in-vitro drug-lab conflicts.

Duplicate Therapy Engine.

Embodiments of the PDSME (6) can, but need not necessarily, include a duplicate therapy engine (69) helps clinicians prevent patients from receiving duplicate drug therapies through the deployment of a highly-specific clinical screening of duplicate drug therapies with clinical relevance. The engine helps detect potentially problematic duplications—not simply two drugs in the same therapeutic class, which may be valid.

Allergens Engine.

Embodiments of the PDSME (6) can, but need not necessarily, include a drug allergy engine (70) executable to identify and consolidate information about drugs known to cause significant allergic reactions, cross-sensitivities, and drug intolerances by identifying and helping to avert drug-allergy issues. Drug-allergy screenings also look at certain inactive medication ingredients such as latex and peanuts. A specially developed Allergen Pick List streamlines workflow by giving the user a convenient way to quickly and easily record a patient's allergy, enabling fast and convenient allergy profiling.

Subscriber Device.

Now referring to primarily to FIG. 1, as above described, one or more subscriber devices (2) can be connect with one or more servers (12) of the system (1) through the network (18). In particular embodiments, the subscriber device (2) can take the form of a limited-capability computer designed specifically for communications over the network (18). Alternatively, the subscriber devices (2) might be a set-top box, an intelligent television connected to receive data through an entertainment medium such as a cable television network or a digital satellite broadcast, a hand-held device such as a smart phone, a slate or pad computer, a personal digital assistant or camera/cell phone, or a multiprocessor system, a microprocessor-based or programmable consumer electronic, a network personal computer, a minicomputer, a mainframe computer, or the like. Each of the one or more subscriber devices (2) can further include other peripheral output devices (71) such as speakers and printers; although the peripheral output devices (71) are not so limited. Each subscriber devices (2) can include an Internet browser (72) such as Microsoft's INTERNET EXPLORER®, GOOGLE CHROME®, MOZILLA®, FIREFOX®, or the like, which functions to download and render multimedia content that is formatted in "hypertext markup language" (HTML).

The Subscription Plan.

Subscriber devices (2) used with the network (18) operate under a subscription plan (3) that define the terms, features, and fees under which network (18) use is granted. For example, a subscription plan (3) might allow a predefined number of requests of the PDSME (6).

Graphical User Interface Module.

Figure 4:
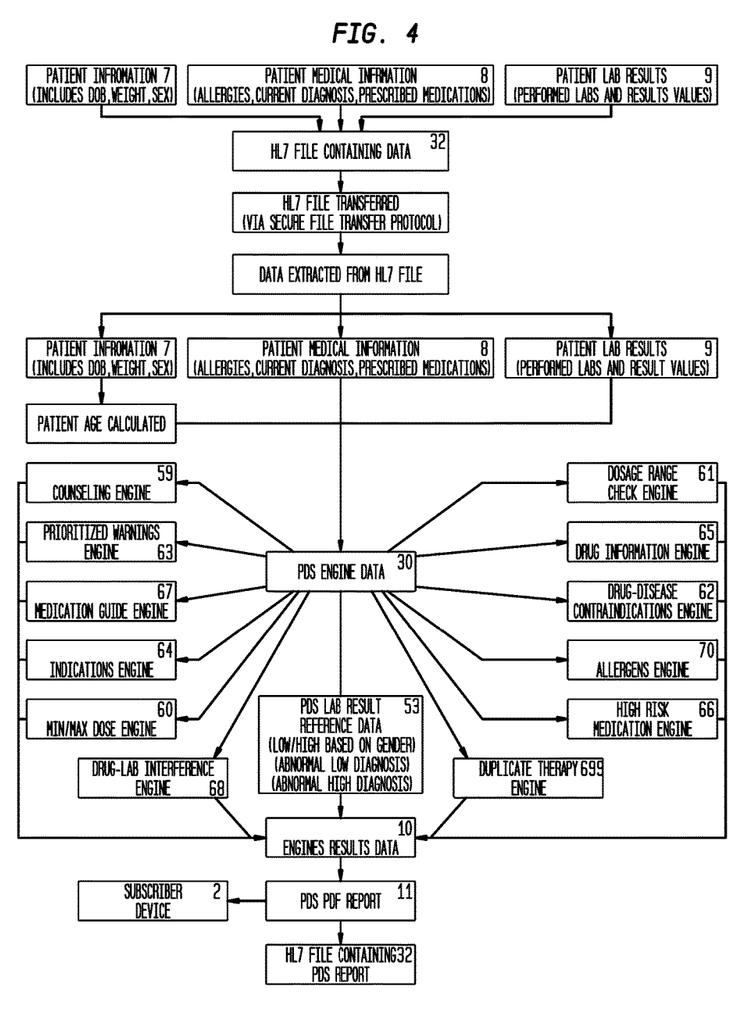
FIG. 4 is a block diagram of a proactive disease state management engine executable to evaluate and score the data in an electronic medical record and output engine results.
Figure 5:
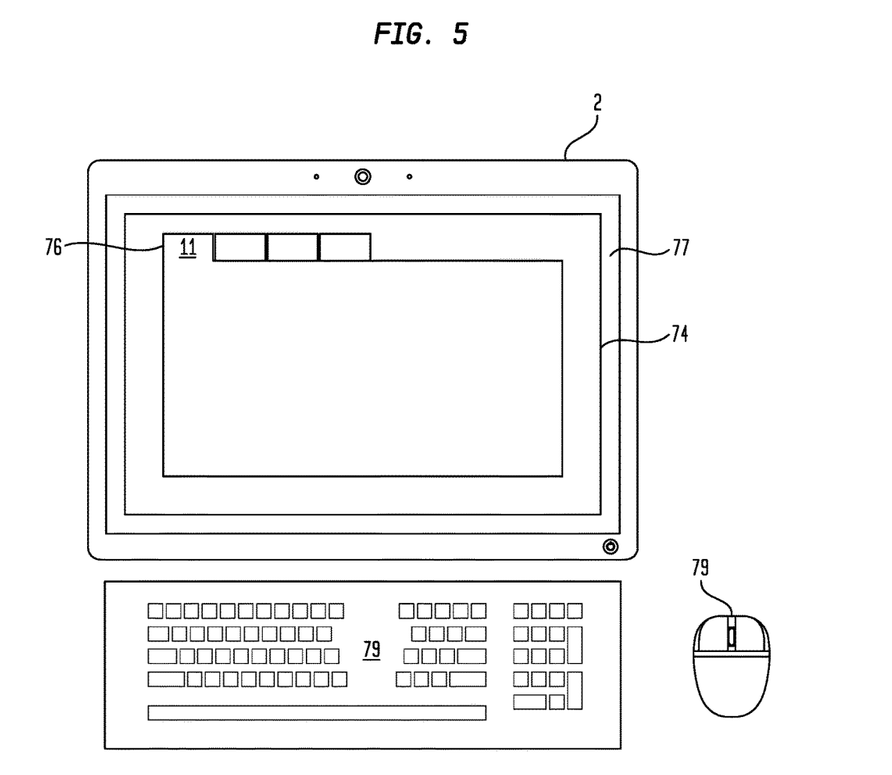
FIG. 5 is an illustration of a subscriber device having a display surface on which menus of a graphical user interface downloadable from the proactive disease state management engine can be displayed.

Now referring primarily to FIGS. 1 and 5, embodiments of the PDSME (6) further include a graphical user interface module (73). The graphical user interface module (73) can be resident in the one or more servers (12) of the system (1) (as shown in the example of FIG. 1) and, as to particular embodiments, the subscriber device (2) can use the Internet browser (72) to simply display downloaded a graphical user interface (74) on the display surface (75) of the subscriber device (2) and to relay user inputs back to the one or more servers (12). The server (12) would respond by formatting or populating one or more graphical user interface menus (76) (see for example FIG. 4) and downloading them for display on the display surface (77) of the subscriber device (2).

In other embodiments, the one or more servers (12) can be used primarily as sources of images and data, with primary responsibility for implementing the graphical user interface (74) being placed upon each of the one or more subscriber devices (2)(as shown in the example FIG. 4). As to these embodiments, each of the one or more subscriber devices (2) can run the graphical user interface module (73) implementing the graphical user interface (74), to retrieve images and data from the one or more servers (12). While illustrative examples in this description attribute images and data to one or more servers (12) for clarity, it is to be understood that various types of images and data may reside in one server computer (12) or can be distributed among a plurality of server computers (12).

It can be appreciated that the PDSME (6) or portion of the PDSME (6) such as the graphical user interface module (73) can be contained and provided on a computer-readable media (78) that can store data that is accessible by the subscriber device (2), such as magnetic cassettes, flash memory cards, digital video disks, Bernoulli cartridges, random access memories (RAMs), read only memories (ROMs), and the like.

A subscriber (79) can enter commands and information into the subscriber device (2) through the graphical user interface (74) through input devices (79) such as a keyboard or a pointing device such as a mouse; however, any method or device that converts subscriber (79) action into commands and information can be utilized including, but not limited to: a microphone, joystick, game pad, touch screen, or the like.

A "click event" occurs when the subscriber (80) operates an PDSME (6) function through the use of a command which for example can include pressing or releasing the left mouse button while a pointer is located over a control icon (or other interactive field which activates a function) displayed in the graphic user interface (74). However, it is not intended that a "click event" be limited to the press and release of the left button on a mouse while a pointer (is located over a control icon (or field), rather, a "click event" is intend to broadly encompass a command by the user through which a function of PDSME (6)(or other program, application, module or the like) including the graphical user interface module (73) which implements the graphic user interface (74) can be activated or performed, whether through selection of one or a plurality of control icon or fields, or by user voice command, keyboard stroke, mouse button, touch on a touch screen, or otherwise.

Again, referring primarily to FIG. 4, showing an exemplary embodiment of the graphic user interface (74) which can be implemented using various technologies and different devices, depending on the preferences of the designer and the particular efficiencies desired for a given circumstance. By click event the subscriber (80) can operate the functionalities of the graphical user interface module (73) to display an interactive graphic user interface (74) on a display surface (77) of the subscriber device (2).

As can be easily understood from the foregoing, the basic concepts of the present invention may be embodied in a variety of ways. The invention involves numerous and varied embodiments of a computer implemented proactive disease state management system and methods for making and using such computer implemented proactive disease state management system including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "trigger" should be understood to encompass disclosure of the act of "triggering"—whether explicitly discussed or not—and, conversely, were there effectively disclosure of the act of "triggering", such a disclosure should be understood to encompass disclosure of a "trigger" or even a "means for triggering." Such alternative terms for each element or step are to be understood to be explicitly included in the description.

In addition, as to each term used, it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the systems or engines herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A method in a computer implemented system, comprising:
    retrieving an electronic medical record from an electronic medical records database;
    identifying each International Statistical Classification of Diseases and Related Codes ("ICDC") and each Nation Drug Code ("NDC") in said electronic medical record;
    comparing each said ICDC and each said NDC in said electronic medical record to a plurality of disease states in a disease state database;
    identifying matches between said ICDC and said NDC in said electronic medical record to said plurality of disease states in a disease state database;
    scoring said electronic medical record based upon matches of said ICDC or said NDC with said plurality of disease states in said disease state database;
    attributing a null score value to each failure to match said ICDC in said electronic medical record to one of said plurality of disease states in said disease state database;
    attributing a positive score value to each match of said ICDC in said electronic medical record to one of said plurality of disease states in said disease state database;
    attributing a null score value to each failure to match said NDC in said electronic medical record to one of said plurality of disease states in said disease state database or if said NDC matches one of said plurality of disease states in said disease state database and further matches a treatment associated with said ICDC matched to one of said plurality of disease states in said disease state database;
    attributing a positive score value to each match of said NDC in said electronic medical records to one of said disease states in said disease state database, if said NDC further matches an adverse effect associated to said disease state;
    attributing a positive score value to each match of said ICDC to one of said plurality disease states in said disease state database if said NDC does not further match a treatment associated with said disease state; and
    generating an aggregate health score by aggregating each said positive score value, said aggregate health score indicative of a health level based on said medical record.

2. The method of claim 1, further comprising:
    comparing said aggregate health score to an average aggregate health score associated with a plurality of electronic medical records of a plurality of patients; and
    assigning said aggregate health score to a risk level based on said comparison of said aggregate health score to said average aggregate health score.

3. The method of claim 2, further comprising:
    associating an upper tri-tile of said aggregate health scores to a high risk level;
    associating a middle tri-tile of said aggregate health scores to a median risk level; and
    associating a lower tri-tile of said aggregate health scores to a nominal risk level.

4. A computer implemented system, comprising:
    a processor communicatively coupled to a non-transitory computer readable media;
    a disease state database including a plurality of diseases states, wherein each of said plurality of disease states referenced to one or more International Statistical Classification of Diseases and Related Codes ("ICDC") and one or more National Drug Codes ("NDC");
    a program contained in said a non-transitory computer readable media, said program including:
        an electronic medical record interface executable to access electronic medical records in one or more medical records databases;
        an electronic medical records evaluation module executable to:
            identify each said ICDC and each said NDC in said electronic medical records;
            compare each said ICDC identified in said electronic medical records to one or more said ICDC associated with each of said plurality of disease states in said disease state database;
            identify matches between said ICDC in said electronic medical record to said plurality of disease states in a disease state database;
            compare each said NDC identified in said electronic medical records to said one or more said NDC associated with each of said plurality of disease states in said disease state database; and
            identify matches between said NDC in said electronic medical record to said plurality of disease states in a disease state database;
        a scoring module executable to:
            score said electronic medical record based upon matches of said ICDC and said NDC with said plurality of disease states in said disease state database;
            attribute a null score value to each failure to match said ICDC in said electronic medical record to one of said plurality of disease states in said disease state database;
            attribute a positive score value to each match of said ICDC in said electronic medical record to one of said plurality of disease states in said disease state database;
            attribute a null score value to each failure to match said NDC in said electronic medical record to one of said plurality of disease states in said disease state database or if said NDC matches one of said plurality of disease states in said disease state database and further matches a treatment associated with said ICDC matched to one of said plurality of disease states in said disease state database;
            attribute a positive score value to each match of said NDC in said electronic medical records to one of said disease states in said disease state database, if said NDC further matches an adverse effect associated to said disease state;

attribute a positive score value to each match of said ICDC to one of said plurality disease states in said disease state database if said NDC does not further match a treatment associated with said disease state; and aggregate each positive score value to generate an aggregate health score.

5. The system of claim 4, further comprising a patient risk level assignment module executable to compare said aggregate health score to an average aggregate health score associated with a plurality of electronic medical records of a plurality of patients.

6. The system of claim 5, wherein said patient risk level assignment further executable to:

associate an upper tri-tile of said aggregate health scores to a high risk level;

associate a middle tri-tile of said aggregate health scores to a median risk level; and associate a lower tri-tile of said aggregate health scores to a nominal risk level.

* * * * *

UNITED STATES PATENT AND TRADEMARK OFFICE
CERTIFICATE OF CORRECTION

| | | |
|---|---|---|
| PATENT NO. | : 10,311,977 B2 | Page 1 of 1 |
| APPLICATION NO. | : 15/898135 | |
| DATED | : June 4, 2019 | |
| INVENTOR(S) | : Randy Blane Huff and William Glynn Day | |

It is certified that error appears in the above-identified patent and that said Letters Patent is hereby corrected as shown below:

On the Title Page

The Name of the Assignee (73):
"Huff & Enterprises, LLC"
Should read:
--Huff & Day Enterprises, LLC--.

Signed and Sealed this
Twenty-ninth Day of October, 2019

Andrei Iancu
*Director of the United States Patent and Trademark Office*